United States Patent

Muller

[11] Patent Number: 5,885,289
[45] Date of Patent: Mar. 23, 1999

[54] PULLER FOR CORRECTING AN UPPER JAW

[76] Inventor: Paul A. Muller, CH-8034, Zurich, Switzerland

[21] Appl. No.: 730,302

[22] Filed: Oct. 11, 1996

[30] Foreign Application Priority Data

Oct. 14, 1995 [DE] Germany .................. 195 38 323.0

[51] Int. Cl.$^6$ .................................................. A61B 17/80
[52] U.S. Cl. .............................................. 606/71; 606/69
[58] Field of Search ................. 606/69, 70, 71, 606/72, 73, 57, 58, 54, 60, 86, 105, 103

[56] References Cited

U.S. PATENT DOCUMENTS

| | | | |
|---|---|---|---|
| 3,473,528 | 10/1969 | Mishkin et al. | 606/57 |
| 3,680,553 | 8/1972 | Seppo | 606/71 |
| 4,565,193 | 1/1986 | Streli | 606/69 |
| 4,957,496 | 9/1990 | Schmidt | 606/70 |
| 4,988,349 | 1/1991 | Pennig | 606/58 |
| 5,129,903 | 7/1992 | Luhr et al. | 606/71 |
| 5,324,291 | 6/1994 | Ries et al. | 606/71 |
| 5,364,396 | 11/1994 | Robinson et al. | 606/53 |
| 5,439,465 | 8/1995 | Tumibay | 606/105 |
| 5,540,687 | 7/1996 | Fairley et al. | 606/60 |

*Primary Examiner*—Guy V. Tucker
*Attorney, Agent, or Firm*—Bachman & LaPointe, P.C.

[57] ABSTRACT

In a puller for correcting an upper jaw (19) on a skull (20), for eliminating an overbite, crossbite, or cleft palate for example, a basic body (11) is provided with elements (4, 18, 22) for attachment to upper jaw (19) and is movable in correction direction ($x_1$).

10 Claims, 2 Drawing Sheets

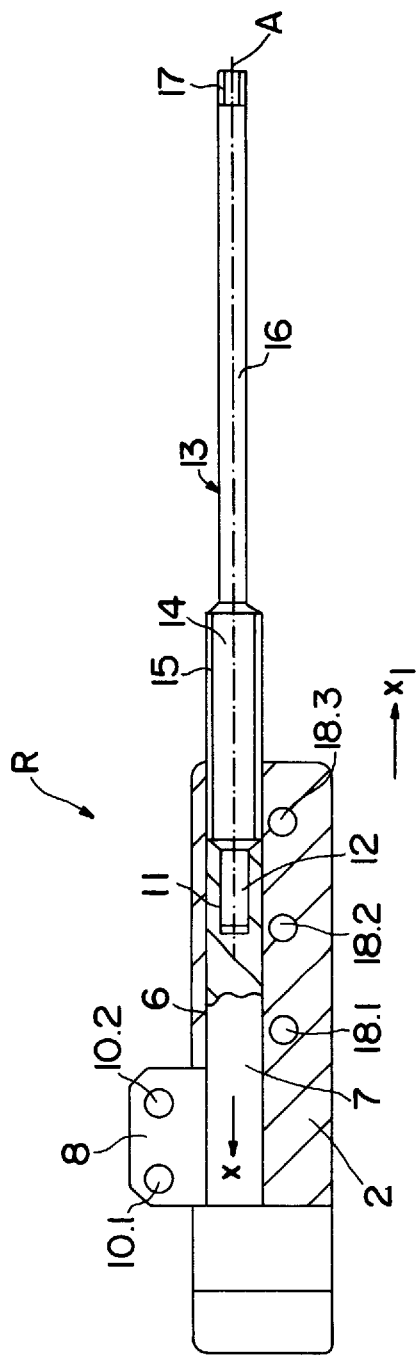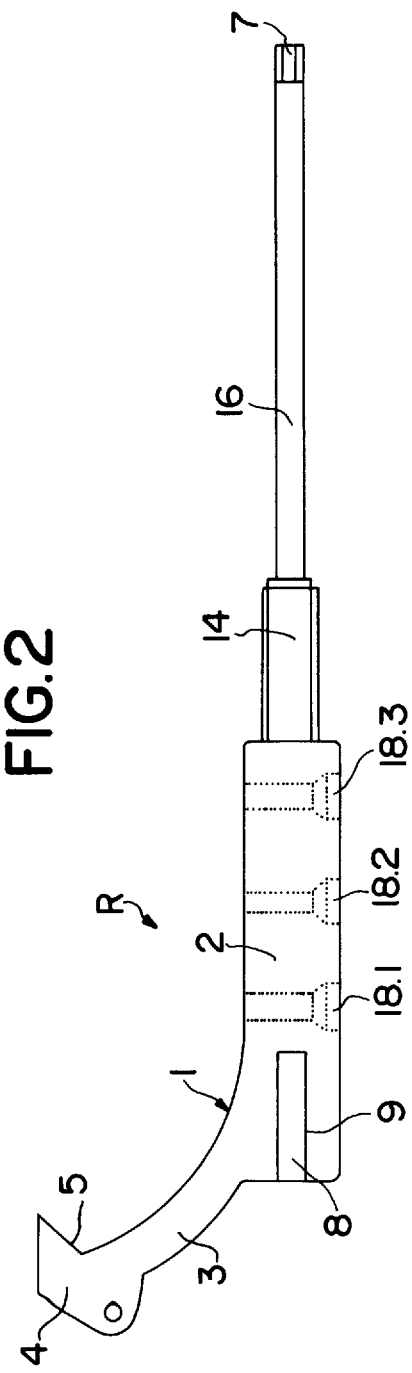

PULLER FOR CORRECTING AN UPPER JAW

BACKGROUND OF THE INVENTION

The invention relates to a puller for correcting an upper jaw in a skull, for example to eliminate an overbite, crossbite, or cleft palate.

Corrections to the upper jaw, especially to achieve occlusion, are usually performed today in Le Fort's operation. This operation lasts approximately 2–3 hours and can only be performed on an in-patient basis; a hospital stay is required.

In the Le Fort operation, the upper jaw is separated completely from the skull and the nasal mucosa is separated as well; the upper jaw is shifted forward and usually secured by titanium plates.

Apart from the costly surgery required, there is often the disadvantage that the jaw, despite the attachment, drops back so that another operation is required.

The present invention has as its goal the development of an above-mentioned puller in which outpatient treatment is sufficient and the risk of the jaw dropping back does not occur.

SUMMARY OF THE INVENTION

To achieve this goal, a basic body is provided with elements to attach it to the upper jaw and is movable in the correction direction.

This means that it is no longer necessary to separate the upper jaw, but instead a correction of the upper jaw is possible using the puller in the course of time. Since this correction proceeds slowly, the upper jaw becomes "accustomed" to its new position, so that the risk of the jaw subsequently dropping back is completely eliminated. The puller is installed in an outpatient operation that does not last longer than one-half to one hour.

The patient can set and adjust the puller himself so that another visit to the hospital is not required.

As a rule, the puller according to the invention is used for forward correction of the upper jaw. However, the idea of the invention is also intended to include the possibility of a rearward correction of the upper jaw, for which purpose appropriate fastening means must be selected.

In addition, a puller can be mounted on one side of the upper jaw, or one puller could be mounted on each side, so that a uniform displacement of the upper jaw forward or, in exceptional cases, rearward is possible.

In a preferred embodiment, a hook on a shaft to grip the upper jawbone above the last molar is provided to anchor the basic body. Preferably, the shaft is connected integrally by an arc with a hook, with the arc and hook forming an undercut that receives the cheek bone in the operating position. In this way, a good pull is exerted to push the cheek bones forward.

It is also possible to attach the basic body to the upper jaw by appropriate fastening elements. Preferably screws are used that traverse corresponding transverse bores and are screwed into the upper jawbone. In a preferred embodiment, however, both mounts are used, in other words, the basic body is attached to the upper jaw by the screws while at the same time the hook fits around the upper jawbone. This mounting method ensures secure fastening of the puller and at the same time provides the best grip on the upper jawbone in order to pull it forward.

To change the position of the basic body, a through bore is provided in the basic body or the shaft, in which bore a slide is mounted, said slide being movable by an actuating element. This slide is displaceable opposite to the correction direction. This means that, at the moment when the slide is being moved, the basic body or the shaft is moved in the opposite direction. This requires however that the slide remain as immobile as possible, for which reason a tab is provided on it that protrudes from the shaft. A mount is attached to this tab and connects the tab with another part of the upper jaw or the skull. As a result, the tab and/or slide is secured indirectly so that when the actuating element is operated, it is not the tab or the slide that is moved, but the basic body and hence the upper jaw connected with the basic body.

For the sake of simplicity, the mount consists of a wire attached at one end to the tab and at the other end to a titanium plate or the like. The latter is then attached by screws for example to another part of the skull or upper jaw.

The actuating element in the present embodiment is rotatable around its lengthwise axis so that it has a threaded section that turns in the through bore. The threaded section has a corresponding external thread and the through bore has a matching internal thread. However, the actuating element is free to turn with respect to the slides, so that it can push the slide away in the through bore, or pull the basic body in the direction opposite to the slide.

For better centering and/or retention of the actuating element with respect to the slide, the actuating element has a pin on one side of the threaded section, said pin fitting endwise into a blind hole in the slide. This pin also turns freely with respect to the slide.

On the other hand, a rod section is mounted on the threaded section and has a hexagonal head for example. This hexagonal head can be engaged by a suitable tool and the actuating element can be rotated around its lengthwise axis by rotating the tool.

It goes without saying that this actuating arrangement consisting of the slide and the actuating element is only an example. Other methods for moving the basic body in the correction direction also fall within the scope of the invention.

BRIEF DESCRIPTION OF THE DRAWINGS

Additional advantages, features, and details of the invention will be apparent from the following description of preferred embodiments as well as the drawing.

FIG. 1 is a top view of a puller according to the invention;

FIG. 2 is a partially sectioned side view of the puller according to FIG. 1;

DETAILED DESCRIPTION OF PREFERRED EMBODIMENTS

Figure 3:
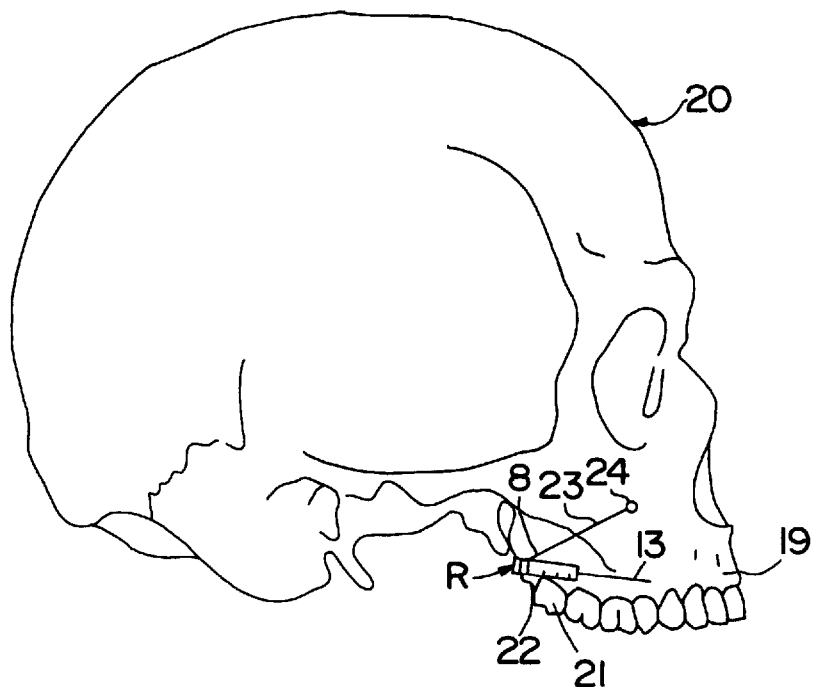
FIG. 3 is a side view of a part of a human skull with the puller mounted.
Figure 4:
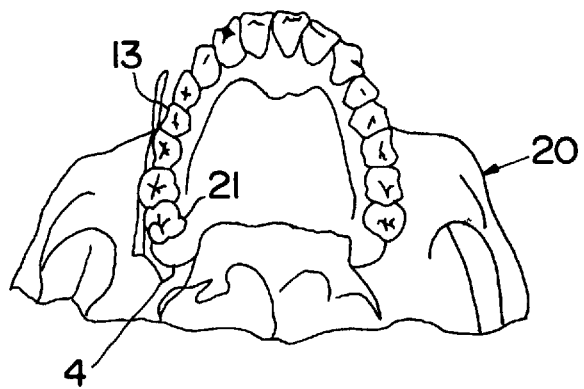
FIG. 4 is a top view of a part of the human skull shown in FIG. 3 in the vicinity of the upper jaw.

A puller R according to the invention, whose function is described in conjunction with FIGS. 3 and 4, according to FIG. 1 has a basic body 1. This basic body 1 consists essentially of a shaft 2 abutted integrally by a hook 4 through an arc 3. This hook 4, together with arc 3, forms an undercut 5 with which puller R, as described below, fits behind the upper jaw (maxilla) on one side.

According to FIG. 2, a through bore 6 is provided in shaft 2, in which bore a slide 7 is received, said slide being movable in the direction of arrow x.

A tab 8 is mounted on one end of slide 7, said tab projecting out of shaft 2 or a shaft slot 9. This tab 8 has two bores 10.1 and 10.2 that receive a retaining element described below.

At the other end of tab 8, slide 7 has a blind hole 11 at the end, into which hole a pin 12 is fitted. Pin 12 rotates freely in blind hole 11 and is part of an actuating element 13 by means of which slide 7 is moved in direction x. For this purpose, actuating element 13 has a threaded section 14 with an external thread 15 that meshes with an internal thread in through bore 6, not shown in greater detail.

A rod section 16 abuts threaded section 14 and terminates in a hexagon 17. If this hexagon 17 is engaged by a matching tool, actuating element 13 can be rotated around its lengthwise axis A so that it rotates freely with respect to slide 7. By means of external thread 15, however, actuating element 13 is screwed further into through bore 6, so that it moves slide 7 in direction x, resulting in an opposite movement of basic body 1 in direction $x_1$.

Three cross bores 18.1, 18.2, and 18.3 pass transversely through lengthwise axis A of shaft 2, said bores serving to receive mounting elements, screws for example, not shown in greater detail.

The function of the present invention is as follows:

According to FIGS. 3 and 4, puller R is mounted on an upper jaw 19 of a human skull 20 in such fashion that hook 4 grips upper jaw 19 behind last molar 21. Then puller R is attached by inserting screws 22 into cross bores 18, with screws 22 passing through cross bores 18 and being screwed into upper jaw 19. Actuating element 13 then runs approximately parallel to upper jaw 19 and/or molars 21.

The holder 23 is connected with tab 8, said holder consisting for example of a piece of wire. This holder 23 is attached at the other end of tab 8 to another point on skull 20, preferably at the cheek bone, with this mount consisting of a titanium plate 24.

If actuating element 13 is then turned, tab 8 moves in direction x, simultaneously causing shaft 2 to move in the opposite direction $x_1$ and move upper jaw 19 forward by means of hook 4. The pressure on upper jaw 19 causes the latter to move forward in the course of time, so that an overbite, cleft palate, or crossbite for example is corrected. In all cases, after a certain period of time, actuating element 13 is rotated further so that in the course of time upper jaw 19 yields to this pressure and moves forward. The end goal is a correct occlusion between the upper and lower jaws.

If it proves necessary, a score can be milled in upper jaw 19 approximately parallel to actuating element 13. However, this is done at only those points where upper jaw 19 offers pressure in opposition to puller R. Normally, this scoring is not necessary.

I claim:

1. Puller for correcting an upper jaw on a skull, which comprises: a basic body portion movable in a first correction direction ($x_1$); elements on said body portion for attachment to the upper jaw; and a longitudinally movable slide carried by said body portion and connected to a holder for attachment to the skull; wherein the basic body portion includes a shaft and a hook to fit behind the upper law, and wherein a through bore is provided in at least one of the basic body and shaft, in which bore said slide is located, and including an actuating element associated with said slide, and wherein said bore has a lengthwise axis and said actuating element has a lengthwise axis essentially parallel to the lengthwise axis of the bore.

2. Puller according to claim 1, wherein the shaft is connected by an arc with said hook, with said arc and said hook forming an undercut.

3. Puller according to claim 1, wherein at least one of the basic body portion and shaft is traversed by at least one cross bore to receive a screw means.

4. Puller according to claim 1, wherein said slide is displaceable opposite correction direction ($x_1$).

5. Puller according to claim 4, wherein a tab is mounted on said slide and projects from said shaft.

6. Puller according to claim 5, wherein said tab is connected to a holder, and wherein said holder is adapted for connection with one of the upper jaw and skull.

7. Puller according to claim 6, wherein said holder is one of a wire and plate, and wherein said holder is connected with a plate which is adapted to be attached to one of the skull and jaw.

8. Puller for correcting an upper jaw on a skull, which comprises: a basic body portion movable in a first correction direction ($x_1$); elements on said body portion for attachment to the upper jaw; and a longitudinally movable slide carried by said body portion and connected to a holder for attachment to the skull; wherein the basic body portion includes a shaft and a hook to fit behind the upper jaw, and wherein a through bore is provided in at least one of the basic body and shaft, in which bore said slide is located, and including an actuating element associated with said slide, and wherein said actuating element has a lengthwise axis and is rotatable around said lengthwise axis, and has a threaded section that rotates in said bore.

9. Puller according to claim 8, wherein said actuating element engages a blind hole in said slide, including a freely rotatable pin in said blind hole, wherein said pin abuts said threaded section.

10. Puller according to claim 9, including a rod section with a hexagonal head which abuts said threaded section.

* * * * *